(12) United States Patent
Smith

(10) Patent No.: US 6,399,664 B2
(45) Date of Patent: Jun. 4, 2002

(54) METHOD OF TREATING CANCER, SPECIFICALLY LEUKEMIA, WITH OZONE

(76) Inventor: Lisa Marlene Jefferys Smith, 23 Gaitwin Street, Brantford, Ontario (CA), N3P 1A9

(*) Notice: Subject to any disclaimer, the term of this patent is extended or adjusted under 35 U.S.C. 154(b) by 0 days.

(21) Appl. No.: 08/984,619

(22) Filed: Dec. 3, 1997

Related U.S. Application Data

(60) Provisional application No. 60/032,332, filed on Dec. 3, 1996.

(51) Int. Cl.[7] .......................... A61K 31/075; A61L 9/04
(52) U.S. Cl. .......................................... 514/715; 424/45
(58) Field of Search .................................. 514/715, 424

(56) References Cited

U.S. PATENT DOCUMENTS 4,632,980 A    12/1986    Zee et al.

FOREIGN PATENT DOCUMENTS

DE    39 40 389    6/1991

OTHER PUBLICATIONS

McGowan et al FEBS Letters Sep. 2, 1996, vol. 392 No. 3 pp. 299–303.*
Zanker et al., In vitro Synergistic Activity of 5–Fluorouracil with Low–Dose Ozone against a Chemoresistant Tumor Cell Line and Fresh Human Tumor Cells *Chemotherapy* 1990:36, pp. 147–154.
Bocci et al., Studies on the Biological Effects of Ozone: 3. An Attempt to Define Conditions for Optimal Induction of Cytokines *Lymphokine & Cytokine Research 12*, 1993, pp. 121–144.
Bocci et al., Autohaemotherapy After Treatment of Blood with Ozone. A Reappraisal *The Journal of International Medical Research 22*, 1994, pp. 131–144.
Viebahn, *The Use of Ozone in Medicine* Karl F. Haug Publishers GmbH & Co, Heidelberg, Germany, 1994, pp. 7–179.
Bocci, Ozone in Medicine Experimental and Scientific Principles From vol. 3 of the Proceedings from 12th World Congress of the International Ozone Association, May 15–18, 1995, Kille, France, pp. 13–27.
Andreesen et al., Selective Sensitivity of Chronic Myelogenous Leukemia Cell Populations to Alkyl–Lysophospholipids *Blood 54*, 1979, pp. 519–523.
Sweet et al., Ozone Selectivity Inhibits Growth of Human Cancer Cells *Science 209*, 1980, pp. 931–933.
Gregory et al., The Role of Colony–Stimulating Factors in Host Defenses *Society for Experimental Biology & Medicine* Mini reviews, 1991, pp. 349–360.
Carpendale et al., Ozone inactives HIV at noncytotoxic concentrations *Antiviral Research 16*, 1919, pp. 281–292.
Cruse and Lewis, Illustrated Dictionary of Immunology, 1995, pp. 168–172.
Bocci et al., Studies of the Biological Effects of Ozone 1. Induction of Interferon on Human Leucocytes et al. *Haematologica 75*, 1990, pp. 510–515.
Ogawa Differentiation and Proliferation of Hematopoietic Stem Cells, *Blood 81*, 1993, pp. 2844–2853.
Clarkson and Strife, Linkage of Proliferative and Maturational Abnormalities in Chronic Myelogenous Leukemia and Relevance to Treatment, *Leukemia 7*, 1993, pp. 1683–1721.
Karlic, *German Cancer Journal 163*, 1987, pp. 37–42.
Kirschner, Ullman's Encyclopedia vol. A18, VCH Verlagsgesellschaft mbH, 1991, pp. 349–357.
Zanker, Proceedings from 2nd International Congress on Neo–Adjuvant Chemotherapy; Paris, 1988, p. 84.
Sartori, Ozone, The eternal purifier of the earth and cleanser of all living beings, *Life Science Foundation B2–B3*, 1994, pp. 64–75.
Kuby, *Immunlogy*, published by W.H. Freeman, New York, New York, 1994.

* cited by examiner

*Primary Examiner*—Geetha P. Bansal
(74) *Attorney, Agent, or Firm*—Eugene J. A. Gierczak

(57) ABSTRACT

A method for treating malignant cells such as leukemia or chronic myeloid leukemia, in a mammal, comprising of administering to the mammal a leukemia therapeutically effective amount of reactive oxygen intermediates. A method of treating cancer in a mammal with cancer and modulating the mammal's immune system, comprising of administering to the mammal in need thereof a cancer therapeutically effective amount of reactive oxygen intermediates. A method of treating leukemia in a mammal with leukemia, comprising of administering to the mammal in need thereof a leukemia therapeutically effective amount of ozone into the mammal's blood and a leukemia therapeutically effective amount of ether lipids.

16 Claims, 14 Drawing Sheets

| Week | Seg. PMN | Band. PMN | Lymphocyte | Monocyte | Eosinophil | Immature |
|---|---|---|---|---|---|---|
| 0 | 111.40 | 71.92 | 11.60 | 23.20 | 7.00 | 7.00 |
| 1 | 220.10 | 46.50 | 15.50 | 9.30 | 9.30 | 9.30 |
| 2 | 174.00 | 93.90 | 73.08 | 0.00 | 3.48 | 0.00 |
| 3 | 135.43 | 62.70 | 7.52 | 2.51 | 5.22 | 32.60 |
| 4 | 128.96 | 40.94 | 12.28 | 14.33 | 6.14 | 2.05 |
| 5 | 126.48 | 28.83 | 11.00 | 5.50 | 5.50 | 3.67 |
| 6 | 115.34 | 23.70 | 7.10 | 6.32 | 1.58 | 1.58 |
| 7 | 143.50 | 39.13 | 0.00 | 0.00 | 6.53 | 19.57 |
| 8 | 88.07 | 30.76 | 4.19 | 1.39 | 2.80 | 9.79 |
| 9 | 123.32 | 15.18 | 6.32 | 7.91 | | 3.16 |
| 10 | 88.80 | 14.40 | 4.80 | 4.80 | 3.60 | 2.40 |
| 11 | 82.00 | 9.00 | 3.00 | 3.00 | 2.00 | 0.00 |
| 12 | 74.90 | 24.19 | 4.60 | 1.15 | 2.30 | 4.60 |
| 13 | 66.70 | 15.15 | 6.06 | 2.02 | 0.00 | 10.10 |
| 14 | | | | | | |
| 15 | 81.78 | 9.68 | 6.46 | 2.15 | 3.23 | 0.00 |
| 16 | 110.00 | 6.10 | 0.00 | 3.60 | 0.00 | 1.20 |

FIG. 14

METHOD OF TREATING CANCER, SPECIFICALLY LEUKEMIA, WITH OZONE

This application claims the benefit of provisional application No. 60/032,332 filed Dec. 3, 1996.

BACKGROUND OF INVENTION

1. Field of Invention

The invention relates to a method for treatment of leukemia in mammals, and more specifically chronic myeloid leukemia (CML), using reactive oxygen intermediates. Reactive oxygen intermediates are administered in a therapeutically effective amount to a mammal that has leukemia. The administration of reactive oxygen intermediates, and more specifically ozone, has been found to be particularly effective in the treatment of CML and on the modulation of the immune and hematopoietic systems of mammals having cancer.

2. Description of Prior Art

Therapeutic usage of ozone has occurred in Europe for more than 50 years. The lack of published data regarding controlled trials as well as mechanisms of explaining it's actions have made ozone therapies almost completely unknown in North America.

Ozone, reactive oxygen intermediates (ROI) or reactive oxygen species (ROS) are known to damage cell membranes and cell proteins. More specifically, in respect of cell proteins, ozone or ROI's exert deleterious effects on amino acids namely, histidine and tyrosine. The mechanisms behind this protein damage have not been fully elucidated. However, it is believed to be related to the chemical reaction between the reactive oxygen radicals hydroxyl radical, hydrogen peroxide, super oxide anion, ($O_2^-$, $H_2O_2$, and OH), (hereafter referred to as ROI) and the chemical bonds in the proteins or amino acids. Most healthy normal cells have anti-oxidant enzymes such as catalase, peroxidase, superoxide dismutase and glutathione, which function to remove or neutralize these oxygen radicals so that no damage occurs. However, it is theorized that ozone and ROI's may cause damage by removing or damaging tyrosine contained in proteins, or by signalling the cell to stop production of protein tyrosine kinases or inhibit the protein tyrosine kinase function which is important for signal transduction as it leads to cell proliferation in normal and transformed cells.

Ozone and ROI's are also known to induce oxidation of cell membrane molecules and have been previously shown to have antineoplastic properties (Viebahn, 1994), more specifically the ability to synergize with chemotherapeutic agents (Zanker, 1988; Zanker and Kroczek, 1990) and radiation (Karlic, 1987). However, the use of ozone and ROI's as an agent in the treatment of cancer has been limited.

Current research suggests that ozone achieves its antineoplastic effects by inducing cell death and inhibiting cell growth in cancerous cells. However, the literature does not indicate the method of cell death. Ozone or ROI induced cell death may be caused by necrosis (typical rupture of cellular membranes), lipid peroxidation, or signalling the cell to commit suicide (called programmed cell death or apoptosis).

In one example, Sweet et al. (1980) examined the effect of ozone on solid tumour masses. The results of these studies indicated ozone can selectively inhibit the growth of cultured human cancerous cell lines derived from lung, breast and uterine solid tumours with little damage to normal cell growth.

Alternative medicine has also referred to the use of ozone or oxygen therapy in reference to cancer and specifically acute T-cell lymphoma (Sartori, 1994). The results of this study demonstrated that ozone in combination with other therapies appeared to have some beneficial effects on the lymphomas and assorted cancers. In general, approximately 50% of the patients died as a result of their aliments. In the surviving patients, there was no clear documentation that ozone or ROI's were the therapeutic agent acting on the cancerous lymphoma. However, Sartori's experiments were concerned with the treatment of 12 lymphoma cases and several of the patients had other complications including AIDS and other cancers. Indeed, clear conclusions were difficult to draw from the Sartori cases as they were not part of a proper control clinical trial and several of the patents also received chemotherapy. Furthermore, the Sartori patients received a variety of alternative medicine treatments called the Life Science Universal (L.S.U.) in combination with ozone.

Neither of these researchers examined the effect of ozone or ROI's on any of the leukemias including chronic myeloid leukemia, nor did they address the use of ozone and ROI's to differentiated cancerous cells as a method of stopping cancer. Indeed, it is well known in cancer research, that the results obtained with one anti-cancer agent in the treatment of one type of cancer, rarely has similar effects in other types of cancer.

Current research has also theorized about the effects ozone has on cytokine levels or cytokine profile. In this respect there is a network or control function for the hematopoietic system which is influenced by a variety of negative and positive stimuli (Gregory et al, 1991; Ogawa, 1993; Kuby, 1994). Negative regulators include interferon alpha, beta, and gamma (IFN-$\alpha$, IFN-$\beta$ and IFN-$\gamma$), tumour necrosis factors alpha and beta (TNF-$\alpha$ and $\beta$) and prostaglandins. Positive regulators of hematopoiesis include the colony stimulating factors (CSF) such a granulocyte/monocyte (GM-CSF), granulocyte (G-SF), monocyte (M-CSF), interleukin-3 (IL-3 or multi-CSF) and stem cell factor (SCF). In addition to the CSFs, other positive regulators of hematopoiesis include IL-1, IL-4, IL-5, IL-6 and IL-11 (Gregory et al, 1991; Ogawa, 1993, Kuby, 1994).

Several studies have shown that ozone increases cytokine levels such as IL-1, IL-2 and IFN-$\gamma$ in humans (Bocci, 1990; Bocci et al., 1993; Bocci, 1994, Bocci, 1995). IL-2 also activates the release of (IFN-$\gamma$) and other regulators which are known to activate the hematopoietic and immune systems (Kuby, 1994; Cruse and Lewis, 1995). None of these studies have examined the effects of ROI's on the immune and hematopoietic systems with respect to cancer and the leukemias.

Another aspect of the abnormalities in leukemia and more specifically CML, is the lack of cell maturation, including cellular enzyme systems and their control mechanisms (Clarkson and Strife, 1993). More specifically, an o-alkyl cleavage enzyme which normally metabolizes alkyl-lysophospholipids or ether lipids is altered or inhibited in leukemia. The accumulation of these alkyl-lysophospholipids such as ET-18-OCH$_3$, interferes with normal phospholipid metabolism and membrane composition resulting in damaged membranes. Normal cells are not adversely affected (Andreesen et al., 1979) by ether lipids as the o-alkyl cleavage enzyme catabolizes the lipids. Previous studies on ether lipids in leukemias did not examine the synergism between ozone or ROI therapy in conjunction with alkyl-lysophospholipids or ether lipids.

Other cancer therapies have focused on bone marrow transplants, but despite improvement of allogenic bone marrow transplant technologies as a means to combat the leukemias, no therapies are currently available for patients who lack a bone marrow donor. Typical maintenance agents such as interferon and hydroxyurea have shown some survival advantage but these therapies are by no means curative. In addition, the toxic side effects of "conventional" chemotherapeutic agents significantly decreases the quality of life, while not necessarily extending it. Once the patient enters the terminal phase of the disease, called blast crisis, there are no treatment options available. It is at this stage that any therapy that provides an extension of life or improves the quality of life is greatly needed.

It would therefore be desirable to provide a method of treatment for leukemia which overcomes the deficiencies of the prior art.

SUMMARY OF INVENTION

It is an object of the present invention to overcome the deficiencies in the prior art treatments of mammals suffering from leukemia such as CML. In accordance with one aspect of the present invention, there is provided a therapy which results in surprising antineoplastic effects in the treatment of leukemia such as CML. More specifically the invention is the administration of a therapeutically effective amount of $O_3$ to the blood of a mammal having leukemia. Preferably, the invention provides treatment for leukemia such as CML, by administering a therapeutically effective amount of ozone so as to induce cellular differentiation of the leukemic cells.

In accordance with a second aspect of the invention there is provided a method of treating leukemia in mammals by administering therapeutically effective amounts of $O_3$ and ether lipids. Preferably, the invention includes the administration of ozone and alkyl-lyophospholipids in therapeutically effective amounts to the blood of mammals having leukemia so as to induce cellular differentiation of the leukemic cells.

In accordance with a third aspect of the invention there is provided a method of treating cancer by administering therapeutically effective concentrations of $O_3$ thereby targeting and/or modulating the hematopoietic and immune systems by the activation of or inhibition of these systems. Preferably, the invention provides that ozone may alter the hematopoietic system through selective targeting and modulating the immune system to combat cancers and leukemias.

In accordance with a fourth aspect of the invention there is provided a method of generating ozone by an ozone generator and administering a therapeutically effective concentration of reactive oxygen intermediates for a period of 5–20 minutes.

With respect to all aspects of the invention the modes of administering reactive oxygen intermediates include but are not limited to: 1. direct injection of gas containing ozone and ROI, 2. ex vivo treatment of blood with ozone and ROI's followed by reinfusion of treated blood, 3. injection of ozonated products, 4. inhalation of ozonated products, 5. insufflation with ozone or ROI gas.

Finally, the invention provides for the generation of ozone and the use of ozone and ROI therapy in a clinical setting to treat mammals having leukemia. Another aspect of the invention is for the use of reactive oxygen intermediates for the production of a medicament for the treatment of leukemia. The administration of ozone and ROI may result in the induction of cell differentiation and maturation of the leukemic blast cells that remain after treatment. This would prove beneficial to the clinical patient by: 1. Reducing the leukemic cell burden on the patent's hematopoietic systems (bone marrow, spleen, and liver) as well as the peripheral blood circulation; 2. Stimulating the immature blast cells to mature and differentiate into normal blood cells; 3. Allowing the differentiation and proliferation of the normal hematopoietic stem cells; and 4. Increasing the psychological and physiological well being of the patient.

BRIEF DESCRIPTION OF FIGURES

FIG. 14 Effects of Ozone on the White Blood Cell Differential Counts from CML Canine #198675 for the period from Sep. 23, 1996 to Jan. 14, 1997.

DETAILED DESCRIPTION OF THE INVENTION

Figure 1A:
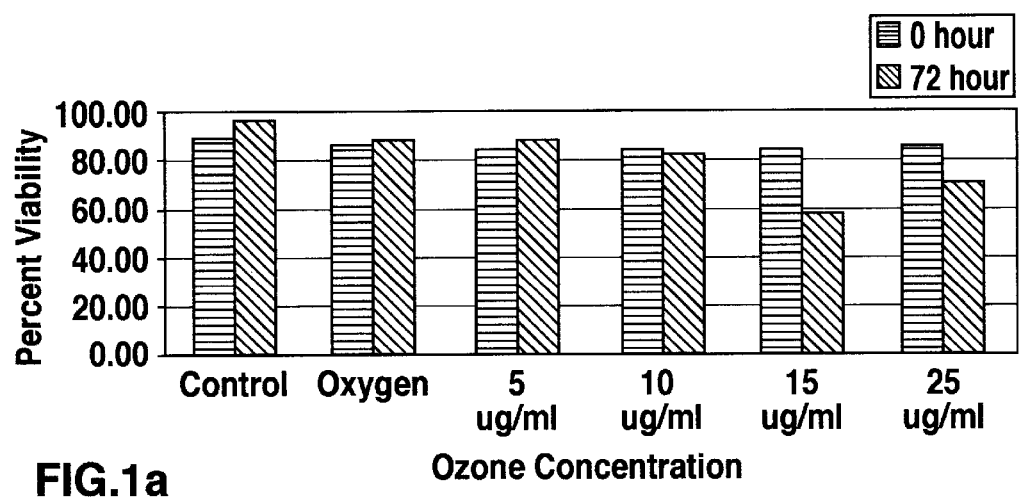
FIG. 1a Effects of Ozone on K562 Viability, Exposure 0.5 minutes.

Leukemia refers to the uncontrolled proliferation of anaplastic leukocytes, present in bone marrow, spleen and in peripheral blood resulting in large numbers of anaplastic leukocytes with various degrees of differentiation and lacking normal cellular functions.

CML involves the proliferation of granulocytes, particularly neutrophils, and the marked enlargement of the spleen. The disease generally runs a mild or chronic course until it changes to a blastic or acute stage. The chronic phase involves the excessive proliferation and accumulation of granulocytes as well as their precursors in both the bone marrow and the blood resulting in an elevated white blood cell count. The disease eventually transforms to the blastic phase and may return to the chronic phase if the subject responds successfully to traditional chemotherapy treatments.

CML was the first neoplasia in which a chromosomal abnormality was observed. The abnormality consisted of a chromosomal translocation of chromosome 9 and 22 in humans which was subsequently named the Philadelphia Chromosome (Ph[1]). Extensive work that followed elucidated many biochemical abnormalities associated with the product of this chromosomal translocation (Clarkson and Strife, 1993). The abnormal protein transcribed from Ph[1] (p210$^{Bcr/Abl}$) possesses intrinsic tyrosine kinase activity whose substrates include key regulators of transduction pathways. The phosphorylation of these substrates results in continuous activation of tyrosine kinase in the leukemic cell which inhibits differentiation, i.e. it does not mature into a normal white blood cell. Development of chemotherapeutic agents has attempted to target these abnormally active enzymes.

Therefore leukemic cells differ significantly from the type of cancer cells studied by Sweet et al, in that in leukemia, the cancerous abnormality is a genetic translocation of chromosomes 9 and 22 which occurs in the primitive progenitor cells of the hematopoietic tissues (bone marrow) responsible for the production of normal blood cells. The chromosomal abnormality results in increased tyrosine kinase activity which results in uncontrolled proliferation and lack of differentiation of leukocytes. There is no specific chromosomal abnormality in the cancers studied by Sweet et al. Further, the abnormality is in the terminally differentiated cells of lung, breast, and uterine tissue resulting in solid tumour masses all of which were studied by Sweet et al. Furthermore, solid tumours are stationary and localized in distinct anatomical locations prior to malignant metastasis while leukemic cells are mobile and widely disseminated throughout the body.

The acute T-cell lymphoma which was studied in Sartori's work is also fundamentally different from leukemias such as CML, in that lymphoma is generally any malignant tumour of the lymphatic tissues, such as the lymph nodes and the spleen. The damage observed in T-cell lymphoma occurs at a later stage of hematopoietic differentiation and only in the T lymphocyte. In contrast, the cancerous transformation in leukemic cells occurs in the primitive progenitor cell responsible for the production of all blood cells. Leukemia is not a solid tumour like lymphoma.

The use of ROI's or ozone as a treatment for leukemia, such as CML has not been thoroughly examined by the prior art. In contrast to solid tumours such as those studied by Sweet et al., leukemias are more suitable targets for ozone and ROI treatment since the neoplasia resides in the circulatory system. Therefore, ozone and ROI gas or ozonated blood may be administered directly into the blood stream. It is here that the administered ozone and ROI gas or ozonated blood would likely exert its effects.

It is hypothesized that the mechanism of the invention is related in part to ROI altering the amino acids, enzymes and protein conformation or structural damage in the leukemic cells (such as CML), which would in turn induce certain protein synthesis and inhibit synthesis or activation by others, namely the tyrosine kinase family. By turning off the tyrosine kinase family of enzymes you can reduce the proliferation (cell multiplication) of the leukemic cell. It is unclear what the exact mechanism is once the ROI enters the mammal's blood stream. It is believed that the ROI's form a reactive oxygen radical that impacts on amino acids, enzymes and other protein structures resulting in the inhibition of the protein tyrosine kinase. The reactive oxygen radical therefore is produced from the administered ozone or ROI for treatment of the leukemic cells. It is suspected that the reactive oxygen radical is the medicament produced from the use of reactive oxygen intermediates for the treatment of leukemia.

The effects of the administration of the ROI's or ozone and the elimination of the disease in the mammal may also be easily monitored, as the frequency of leukemic progenitors is substantially increased in the bone marrow and in circulation during most stages of the disease.

Methods of ozone or ROI administration which are within the scope of the invention include, but are not limited to: 1. direct injection of gas containing ozone and ROI, 2. ex vivo treatment of blood with ozone and ROI's followed by reinfusion of treated blood, 3. injection of ozonated products, 4. inhalation of ozonated products, 5. insufflation with ozone or ROI gas. Other methods for the application of ozone and ROI's to leukemias including CML will be readily apparent to those skilled in the art and are encompassed within the scope of this invention.

Methods of alkyl-lysophospholipids or ether lipids administration which are within the scope of the invention include, but are not limited to: 1. direct injection of alkyl-lyophospholipids or ether lipids, 2. ex vivo treatment of blood with alkyl-lysophospholipids or ether lipids followed by reinfusion of treated blood, 3. injection of ozonated alkyl-lysophospholipids or ether lipids products, 4. nutritional diet supplement with alkyl-lysophospholipids or ether lipids. Other methods for the application of ether lipids to leukemias including CML will be readily apparent to those skilled in the art and are encompassed within the scope of this invention.

The present invention provides a method of treating leukemia in a mammal by administering a leukemia therapeutically effective amount of reactive oxygen intermediates. As evidenced by the data and results outlined in examples 1 and 2, Applicant has found that the proliferation of leukemic blast cells may be reduced by administering a leukemic therapeutic amount of reactive oxygen intermediates such as ozone in both the in vivo and in vitro settings.

Figure 13:
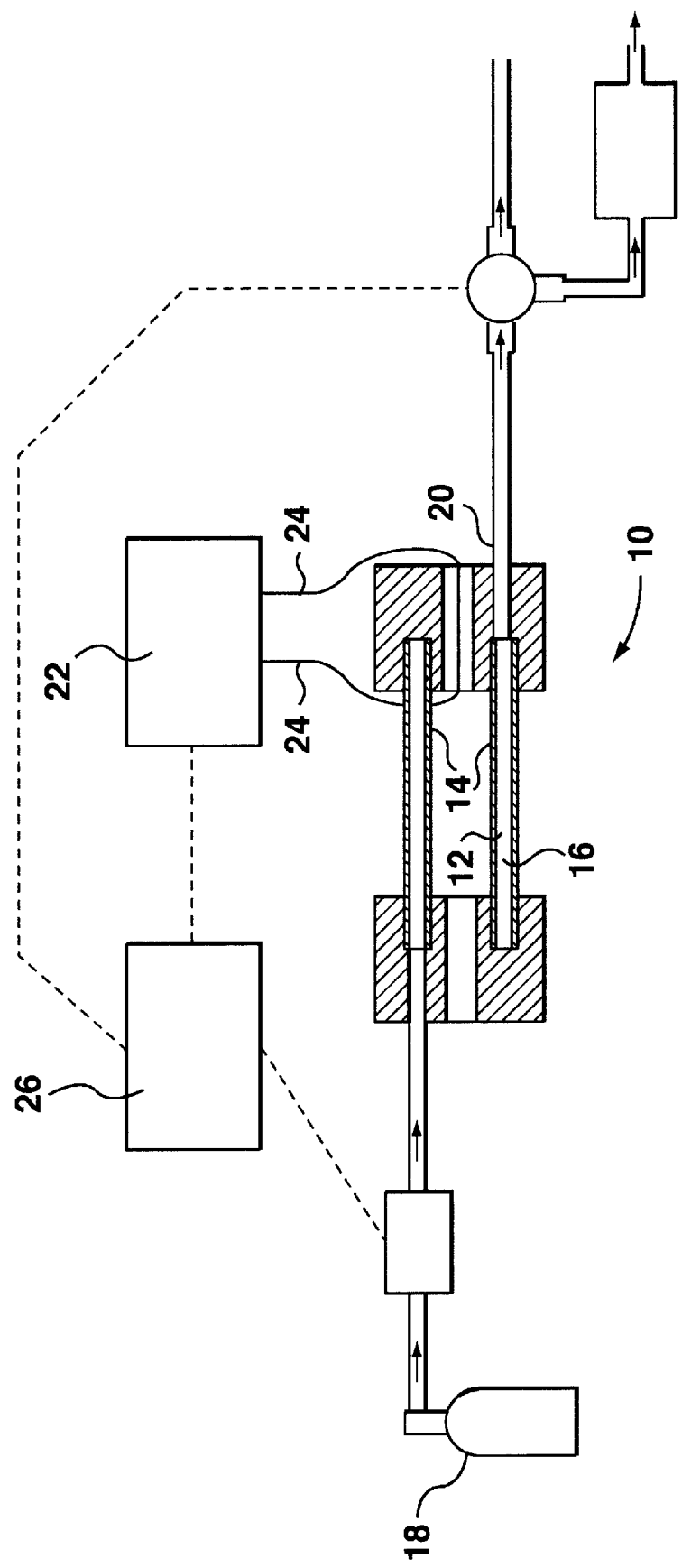
FIG. 13 Basic Ozone Generator Diagram.

Prior to the administration of the ROI or ozone to the mammal, the ozone must first be generated. Referring to FIG. 13, an ozone generator 10 may be based on the silent corona discharge principle, whereby an electrostatic field or corona discharge space 12 is created between a high voltage electrode 14 and a dielectric member 16. From an oxygen source 18, oxygen passes through the corona discharge space 12, wherein a small percentage of oxygen is converted into ozone. The ozone is then released or pushed out a outlet hole 20 and collected for administration in the appropriate concentrations to a mammal. The ozone generator 10 may be connected to a power supply 22 via high voltage leads 24. The frequency and voltage output of the power supply 22 may be controlled by a microcontroller 26. In general, ozone may deteriorate after 20 minutes. Ozone may also be introduced to the blood by a micro-bubbler, in which the ozone gas is bubbled through the blood and then the blood is reinfused back into the subject.

The ozone gas is preferably delivered to the blood of the mammal by direct injection into the mammal's blood stream once the ozone has been generated. Other methods of delivery have already been disclosed. The ozone gas used in connection with the preferred method has a concentration of ozone from about 2 ml/kg of mammalian body weight to less than a toxic amount, and is administered for a period for about 5 to 20 minutes.

In another alternative method, the preferred concentration of ozone delivered to the mammal is from about 2 ml/kg of mammalian body weight to about 20 ml/kg of mammalian body weight for a period of about 5 to 20 minutes.

Another alternative method involves treating leukemia or CML in a mammal by administering a CML therapeutically effective amount of reactive oxygen intermediates and a CML therapeutically effective amount of ether lipids.

Due to the lack of cell maturation with CML, the o-alkyl cleavage enzyme which normally metabolizes ether lipids is inhibited. As a result, these leukemic cells experience an accumulation of the ether lipids. By administering ether lipids such as alkyl-lyophospholipids, ET-18-OCH$_3$, there is a further accumulation of these ether lipids, providing an affiniity for the administration of reactive oxygen intermediates such as ozone. This affinity or synergism between reactive oxygen intermediates and ether lipids, allows for the oxygen intermediates to impact on amino acids, enzymes and other protein structures resulting in the inhibition of the protein tyrosine kinase, thereby allowing cellular differentiation of the white blood cells.

Another method involves treating cancer and modulating the hematopoietic and the immune systems of the mammal by administering a cancer therapeutically effective amount of reactive oxygen intermediates. The effective concentrations range from about 2 ml/kg of mammalian body weight to a less than toxic amount. The use of ozone may alter the hematopoietic and immune systems through selective targeting and modulating the immune system to combat cancers and leukemias. Although ozone is known to have an impact on the cytokine profile, studies have not focused on this impact with respect to cancer or leukemia.

By administering a therapeutically effective amount of reactive oxygen intermediates, when treating leukemia, the cytokine profile is directly impacted by either inhibiting or activating different signals from the immune and hematopoietic systems.

Another alternative method involves lowering the level of white blood cells in a mammal having leukemia by the generation of ozone and the direct injection of reactive oxygen intermediates, such as ozone into the blood stream of the mammal.

The increased proliferation of white blood cells in a mammal having leukemia may be reduced by the administrating a preferred concentration or ozone or ROI's from about 2 ml/kg of mammalian body weight to less than a toxic amount for a period from about 5 to 20 minutes.

The present invention also describes the use of reactive oxygen intermediates for treating leukemia and CML, as well as treating a mammal having cancer and modulating the mammal's hematopoietic and immune systems. An alternative use is to use reactive oxygen intermediates and ether lipids for treating leukemia and CML. These uses are achieved by the methods and examples herein described.

EXAMPLE 1

A 7 year old female Dalmatian canine patient was diagnosed as having chronic myeloid leukemia (CML) and severe diarrhea by the Ontario Veterinary College in July 1995 (CML canine case #198675).

Figure 9A:
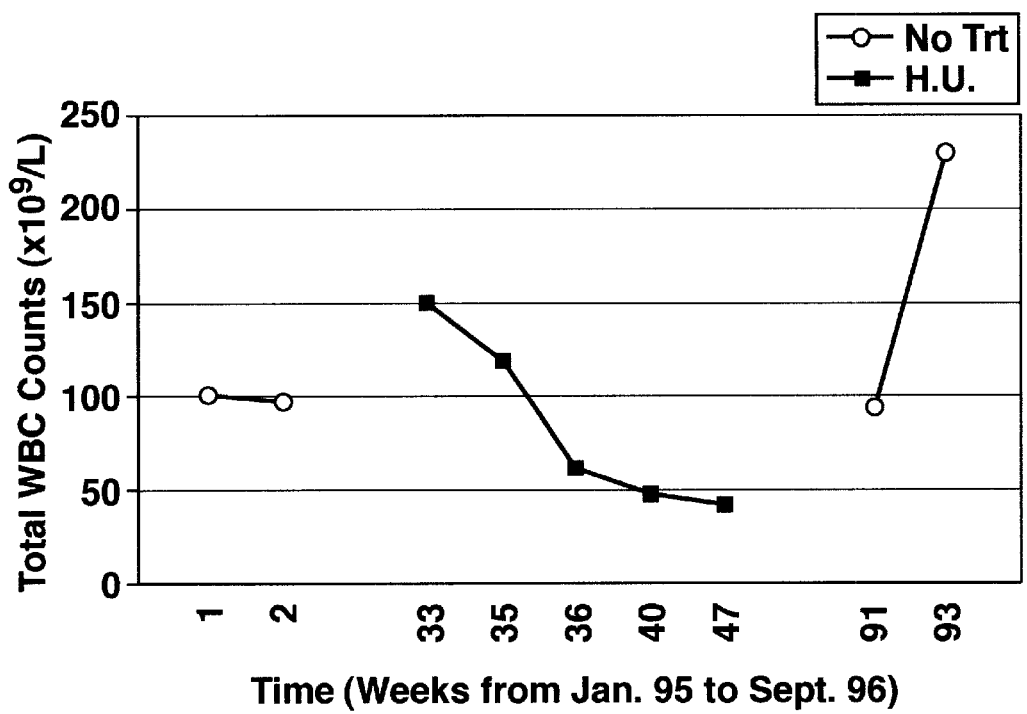
FIG. 9a Effects of Hydroxyurea or No Treatment on WBC from CML Canine #198675.
Figure 9B:
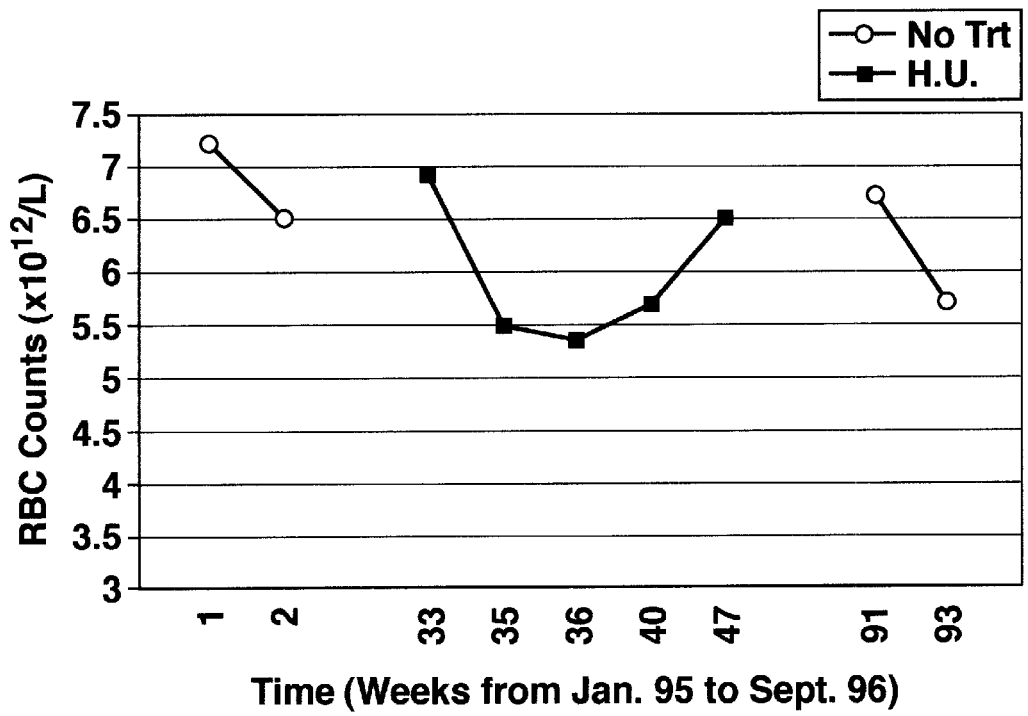
FIG. 9b Effects of Hydroxyurea or No Treatment on RBC from CML Canine #198675.

The patient was originally diagnosed with elevated white blood cell counts (leukocytosis) and an enlarged spleen (splenomegaly) with suspected inflammatory bowel disease (IBD) in January 1995. Referring to FIG. 9a and 9b, the patient did not receive any treatment at that time. FIG. 9a showed elevated total white blood cell (WBC) counts and FIG. 9b showed the effects of the CML tumour on the red blood cell (RBC) levels.

Figure 12:
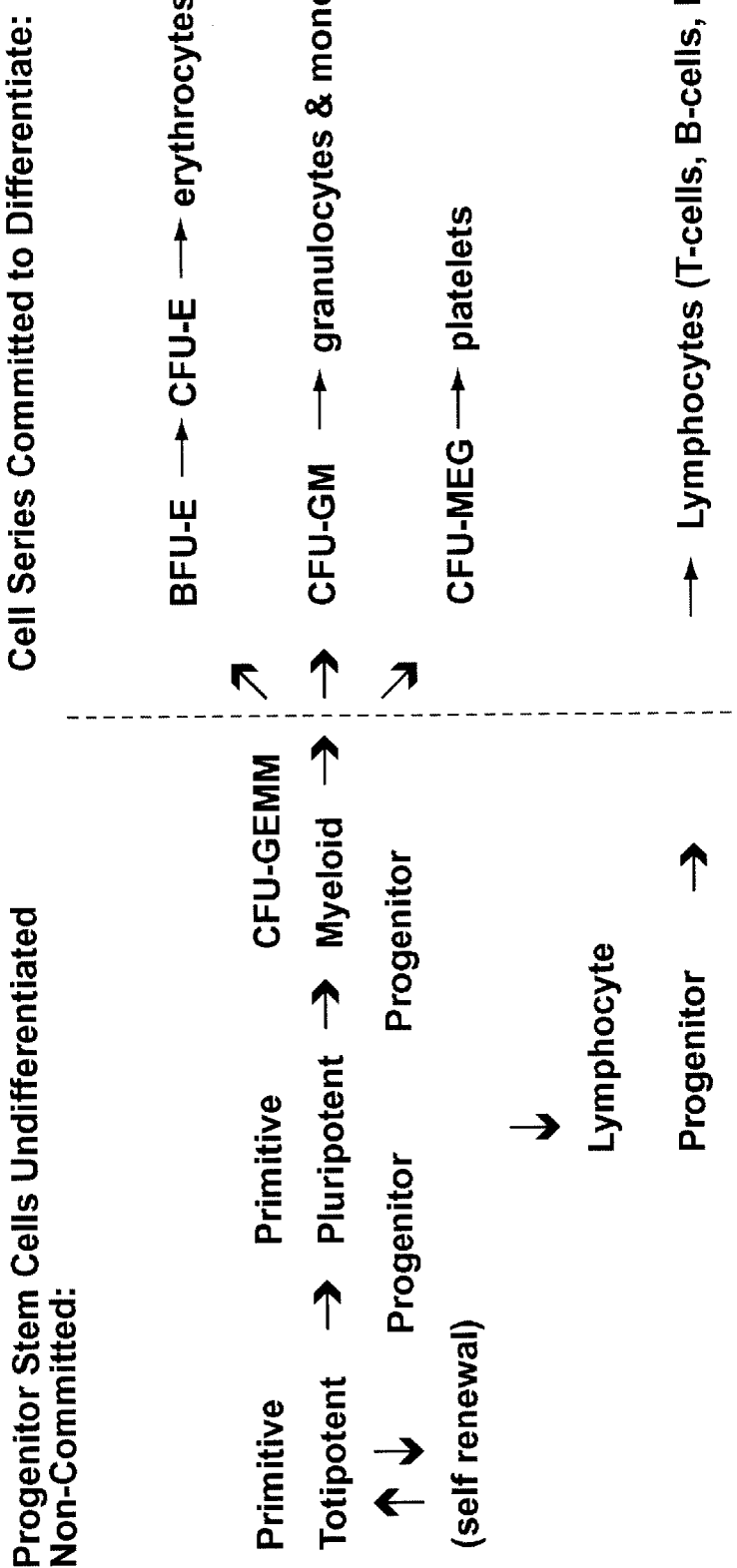
FIG. 12 Hematopoiesis: Production of the Blood Cell Series.

The final stages of leukemia known as 'blast crisis' has extremely high concentrations of immature/primitive progenitor stem cells shown in FIG. 12. With increased tumour growth, blast crisis, the ability of the bone marrow to produce RBC's was impaired and the associated anemia and lethargy were observed in the patient.

In July of 1997, the diagnosis of CML was confirmed by biopsy and pathology at the Ontario Veterinary College (OVC). The patient received conventional chemotherapy in the form of Hydroxyurea (HU; 500 mg twice daily for approximately one year) with a decrease in total WBC counts (FIG. 9a). The WBC levels never returned to the normal canine range of 6.1 to 17.4×10$^9$ cells per liter. However, HU treatment of CML showed signs of improvement (remission) and the RBC counts increased with time as shown in FIG. 9b. The patient clinically presented with the side effects of depression, lethargy, severe to mild diarrhea, anorexia, vomiting, weight loss, occasionally vaginal bleeding, abdominal pain and splenomegaly. After one year of chemotherapy, the owner would not continue with the conventional therapy and stopped the HU treatments. The patient entered blast crisis at 1.5 months after cessation of conventional chemotherapy (September 1996; FIG. 9a). Neither the lymphoma nor the IBD were successfully treated.

The attending veterinarian discussed euthanasia and the ozone or ROI therapy described in this invention with the owner under strict confidence. The owner and all attending veterinarians signed consent and confidentiality forms and the ozone or ROI therapy began on Sep. 23, 1997 and continued for 16 weeks.

1. Materials and Methods

Prior to each weekly ozone or ROI treatment the patient's complete blood counts were measured using a Coulter Counter Hematology Analyzer (Coulter Electronics Canada Co.). The leukocyte differential counts were determined manually by the pathologist and recorded in FIG. 14. Ozone and ROI's were generated from a high voltage corona discharge electrical ozone generator using medical grade oxygen as shown in FIG. 13. Ozone/oxygen gas (30 to 60 ml) was injected intra-venously (iv) through a sterile catheter needle (Abbocath-T, 22 g×1¼ in.; Abbott Ireland) inserted in the leg vein of the mammal (canine #198675) with a sterile extension set (79 cm, E407, Abbott Ireland) attached to the syringe containing the ozone ROI gas mixture. The ozone/oxygen gas mixture was slowly injected over a 10 to 20 minute period to allow maximum gas absorption.

The secondary or adjunct to the preferred route of administration was minor autohemotherapy (minor AHT) where heparinized whole blood (7 ml each treatment) was gently mixed in a disposable syringe or devise with increasing doses of ozone to a maximum of 25 ml at 34 to 42 µg/ml (dose is species specific). The blood gas mixture was allowed to equilibrate at room temperature for 1 to 5 minutes with intermittent mixing. The excess gas was evacuated prior to intramuscular (im) or subcutaneous (sc) injection of the ozonated blood at several locations.

Patients were accessed prior to, during and post treatment by blood tests, clinical response, and biopsy when appropriate.

2. Results

The results of the experiments showed an increase in the patient's quality of life as documented clinically by the owner, the attending veterinarian, and the inventor research scientist. The patient had increased appetite and energy levels, improved attitude and she exhibited normal canine behaviour once again. The owner noticed a decrease in the vomiting after the first two weeks of treatment. There was a slight improvement in the diarrhea, although only temporary.

Figure 10A:
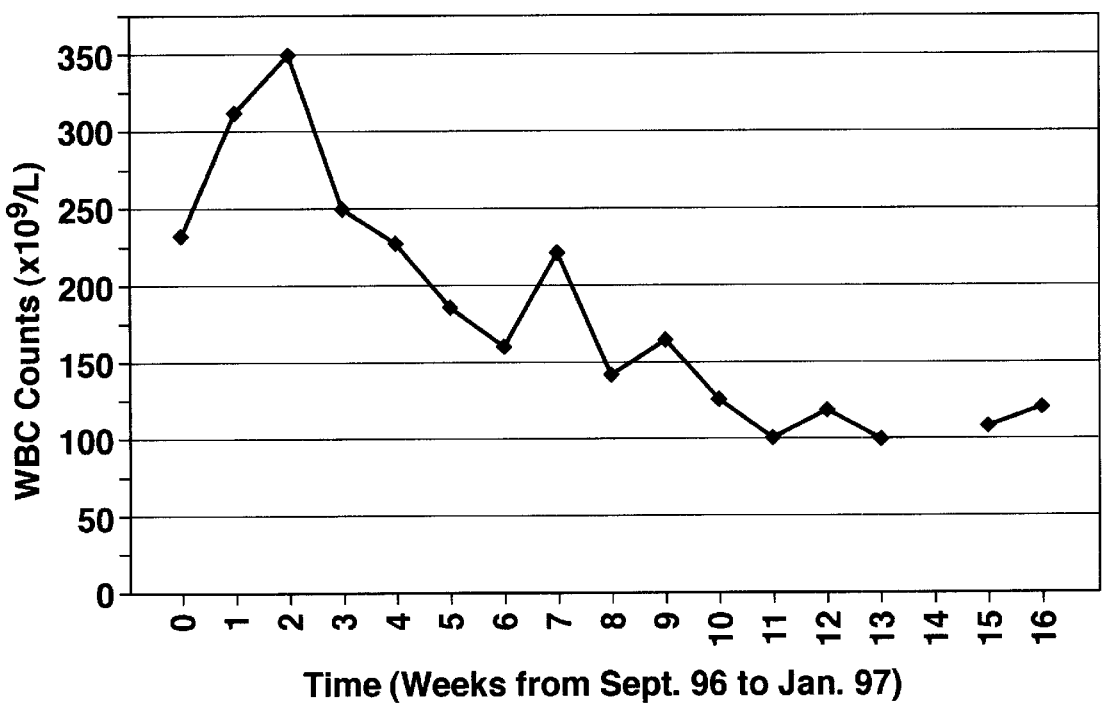
FIG. 10a Effects of Ozone on Total WBC Counts from CML Canine #198675.
Figure 10B:
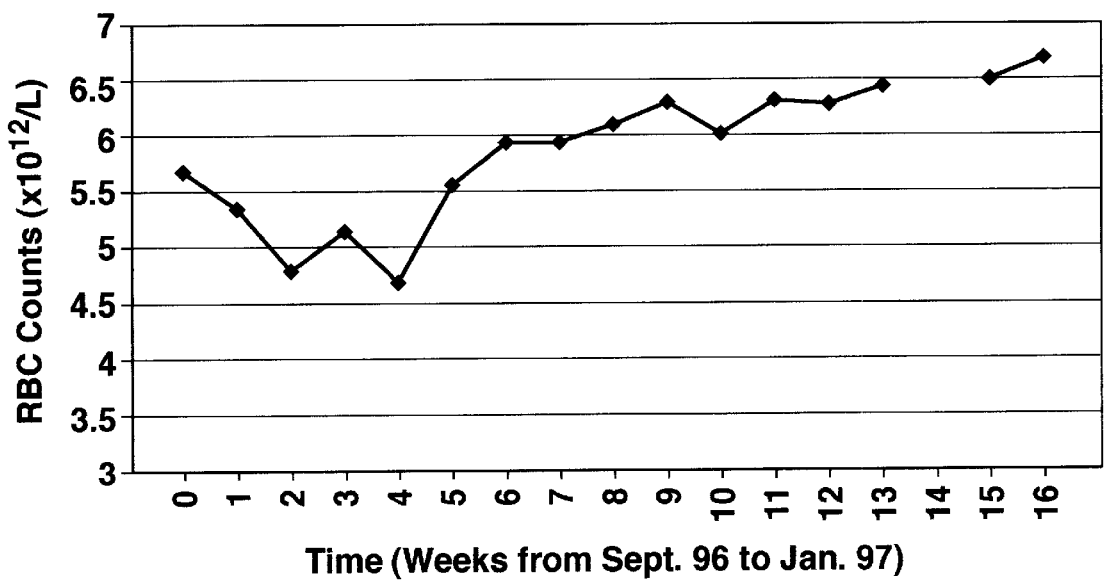
FIG. 10b Effects of Ozone on Total RBC Counts from CML Canine #198675.
Figure 11:
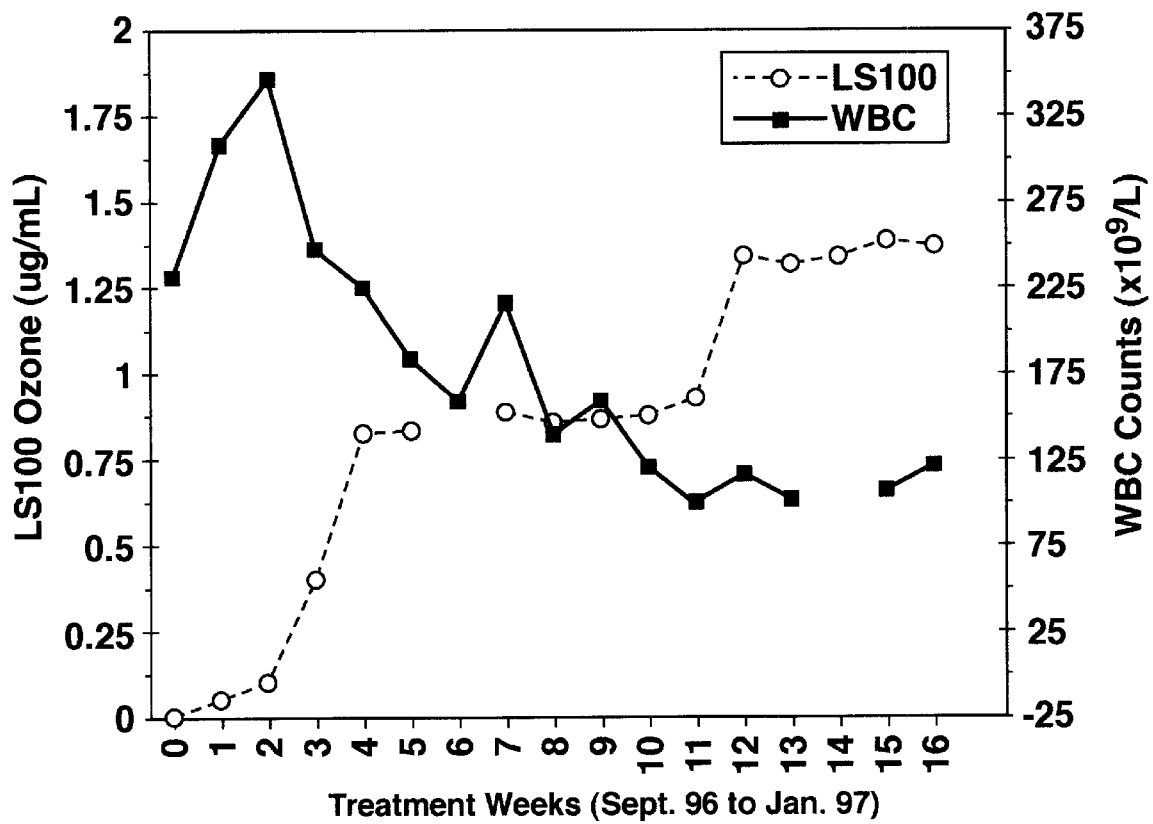
FIG. 11 Dose Response of Ozone on WBC from Canine #198675 with Chronic Myeloid Leukemia.

The experimental results indicated that ozone or ROI's reversed the progression of CML as documented by the total WBC and RBC counts as shown in FIGS. 9–11. The last data entry in FIGS. 9a and 9b corresponds to the first data point in FIGS. 10a and 10b and were considered control or baseline for the patient (CML canine #198675) at the onset of the ozone or ROI therapy. FIGS. 10a and 10b showed the effects of the invention on the CML tumour as monitored by total WBC and RBC counts for the duration of the 16 week treatments. Further evidence of CML remission came from the observed maturation and differentiation of the leukemic WBC's as shown in FIG. 14. The ability of the immature stem cell to differentiate into the different blood cell types as outlined in FIG. 12, was improved with ozone therapy and was also ozone dose dependent (16 to 42 $\mu$g/ml generated ozone concentration). As shown in FIG. 11, the dose of ozone increased with time over the 16 week therapy. A decrease in the total WBC counts were observed with the increase of the internal ozone concentration in the mammal. At the concentrations of ozone injected (16 $\mu$g/ml ozone, up to a maximum of 197 ug total) corresponding to an in vivo concentration of less than 0.25 $\mu$g/ml ozone showed significant activation of the canine hematopoietic system. This ozone induced activation resulted in a significant increase in the production of leukemic cells. At the higher concentrations of ozone injected, between 28 to 42 $\mu$g/ml ozone (up to a maximum of 2100 ug total) corresponded to an in vivo concentration between 0.5 to 1.5 $\mu$g/ml ozone or ROI's. This higher internal ROI ozone level showed significant inhibition of the canine hematopoietic system with a significant reduction in the production of leukemic cells. The results observed in FIG. 11 and FIG. 14 showed the selective modulation of the immune system to combat malignant diseases such as leukemia by the invention.

The diarrhea was not related to the CML, and was later diagnosed upon autopsy to be intestinal lymphoma with an associated inflammatory bowel disease (IBO) by the Ontario Veterinary College, Jan. 14, 1997.

EXAMPLE 2

In order to demonstrate the effects of the invention on leukemias, the K562 cell line as the experimental model for human CML was chosen, and used peripheral blood mononuclear cells (PBMC) from normal patients as the controls. The final stages of leukemia known as 'blast crisis' has extremely high concentrations of primitive (pluripotent) progenitor stem cells (FIG. 12). The K562 is a self renewing cell line which was established from a female patient with CML, in terminal blast crisis. As a result, the K562 cell line is composed of highly undifferentiated primitive progenitor cells that are not committed to any particular cell line series (FIG. 12). Furthermore, the K562 spontaneously produce recognizable progenitors of the granulocytic, monocytic and erythrocytic series. Therefore, the K562 cell line is a reasonable model to use for the study of human leukemias.

b 1. Materials and Methods

Ozone and ROI's were generated using medical grade oxygen from a high voltage corona discharge electrical ozone generator (Carpendale and Freeberg, 1991; Viebahn, 1994; FIG. 13). Liquid RPMI complete media suspension of K562 cell cultures or normal human whole blood (10 ml each treatment) was processed through a micro-bubbling device at several ozone concentrations (5, 10, 15, and 25 $\mu$g/ml). In addition, a 100% oxygen treated and non-processed control samples were also examined. After processing, complete blood counts were measured on all whole blood samples. Peripheral blood mononuclear cells (PBMC) were isolated using a standard density gradient of 1.077 g/ml and washed with Iscove's medium. Viability and cell counts were determined manually using a hemocytrometer and a 4% solution of Trypan blue. Cell concentrations were adjusted to $2.0 \times 10^6$ cells/ml. Cells were mixed in a 1:10 (v/v) ratio with methylcellulose medium with recombinant growth factors (#HCC-4434, StemCell Technologies Inc.) and plated to contain $2 \times 10^5$ cells per plate in duplicate for normal PBMCs and $2 \times 10^4$ for K562 cells. Plates were incubated at 37° C. in a $CO_2/O_2$ incubator. Colonies were scored on day 5, 8, 10 and day 14 according to the scoring criteria by StemCell Technologies. The data results for cell viability, total colonies (proliferation) and individual colony cell types (differentiation) are presented in FIGS. 1–8.

2. Results

Figure 1B:
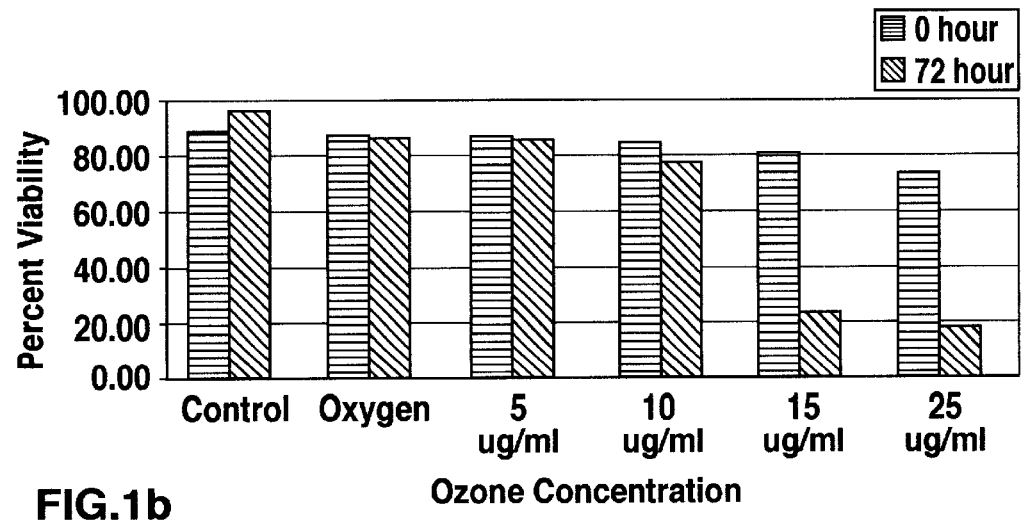
FIG. 1b Effects of Ozone on K562 Viability, Exposure 1.5 minutes.
Figure 1C:
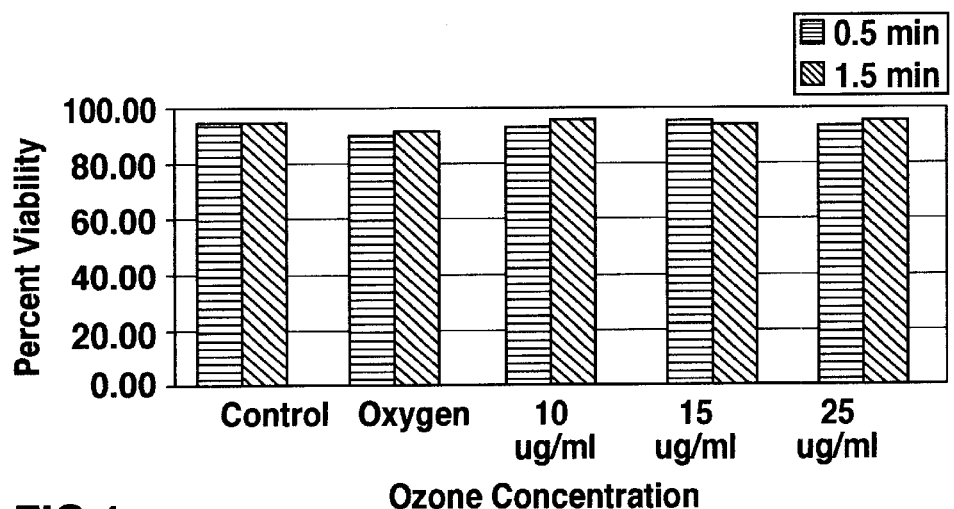
FIG. 1c Effects of Ozone and Exposure Time on Human PBMC Viability.
Figure 2A:
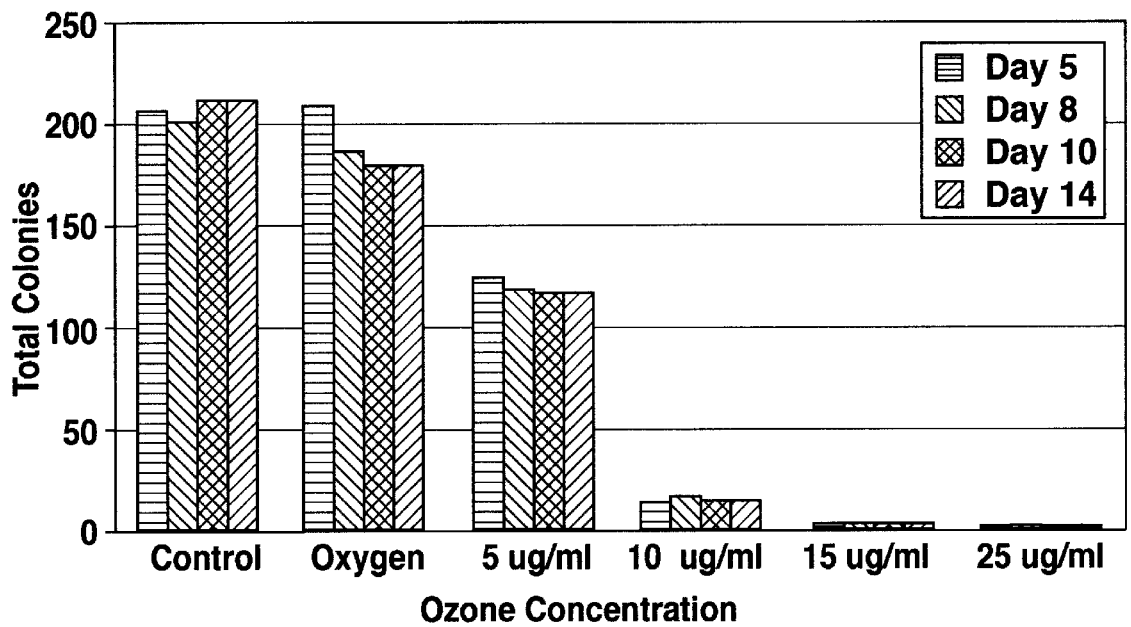
FIG. 2a Effects of 1.5 min. Ozone Exposure on K562 Colony Formation.
Figure 2B:
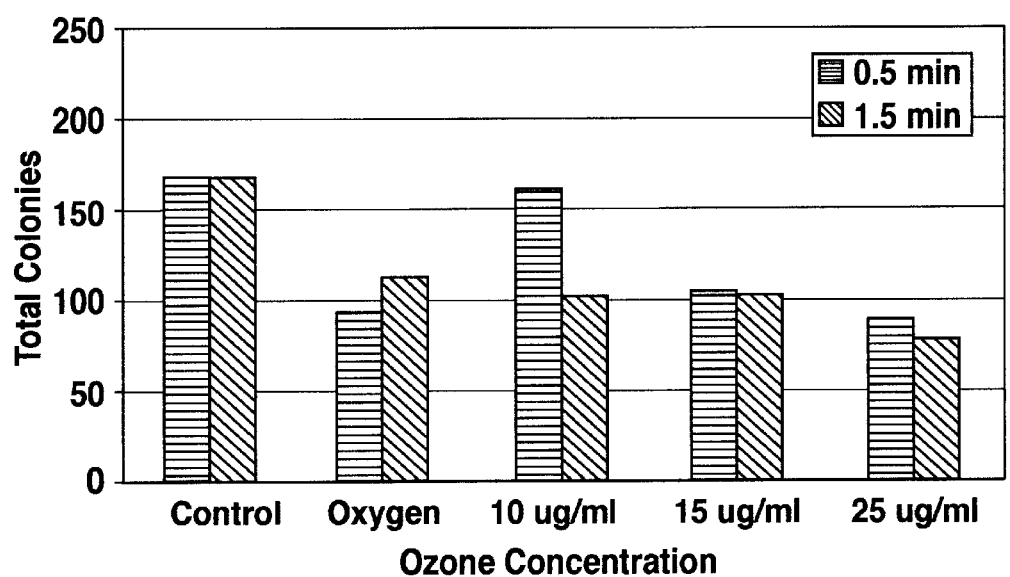
FIG. 2b Effects of Ozone and Exposure Time on Normal Human Colonies.
Figure 3A:
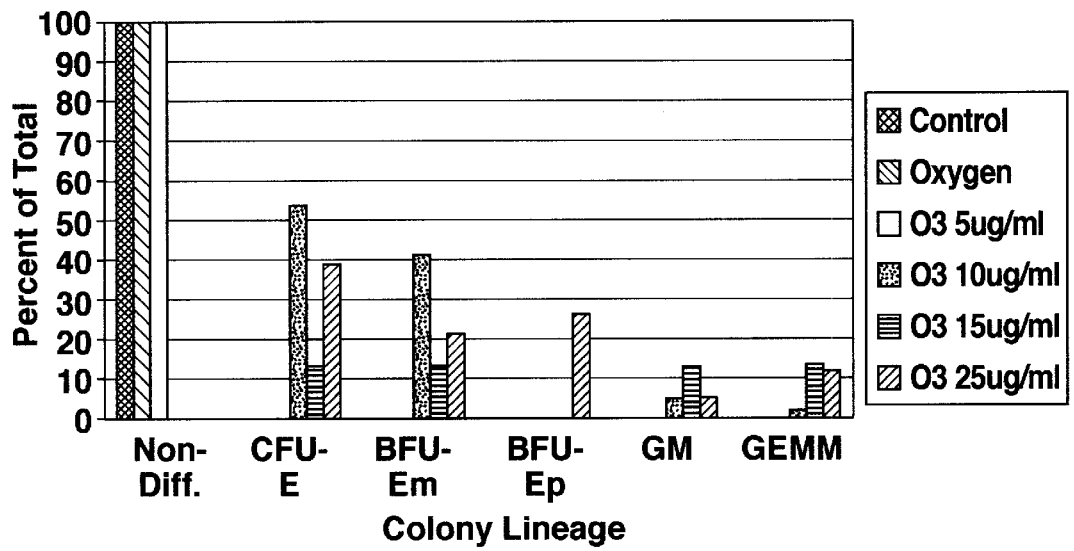
FIG. 3a Effects of Ozone on K562 Colony Differentiation, 1.5 minute Exposure.
Figure 3B:
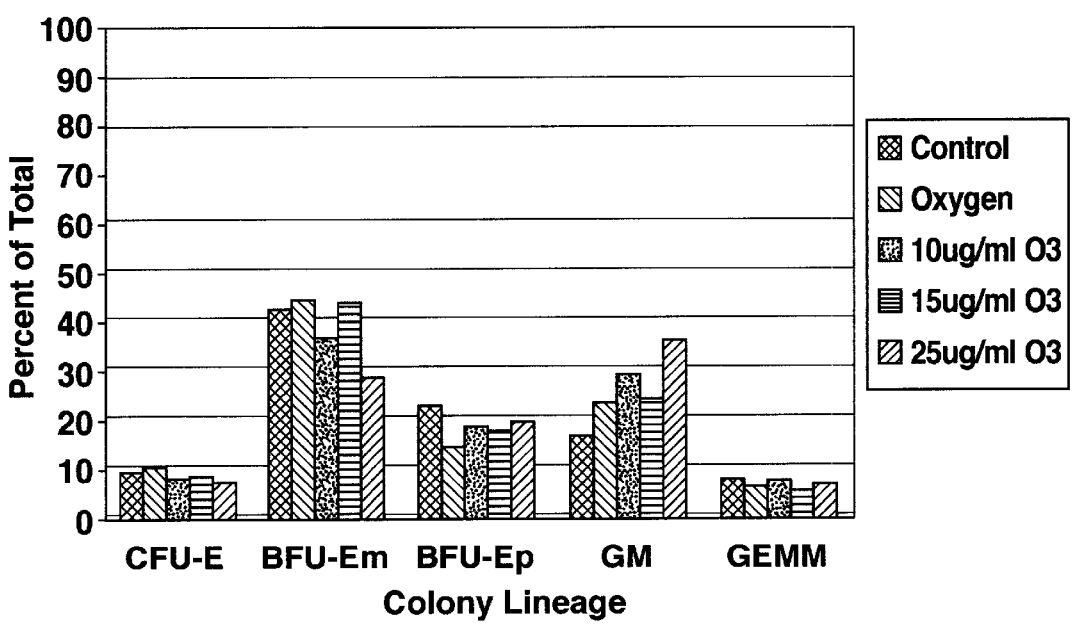
FIG. 3b Effects of Ozone and Exposure Time on Normal Human Colony Differentiation, 1.5 min.
Figure 4A:
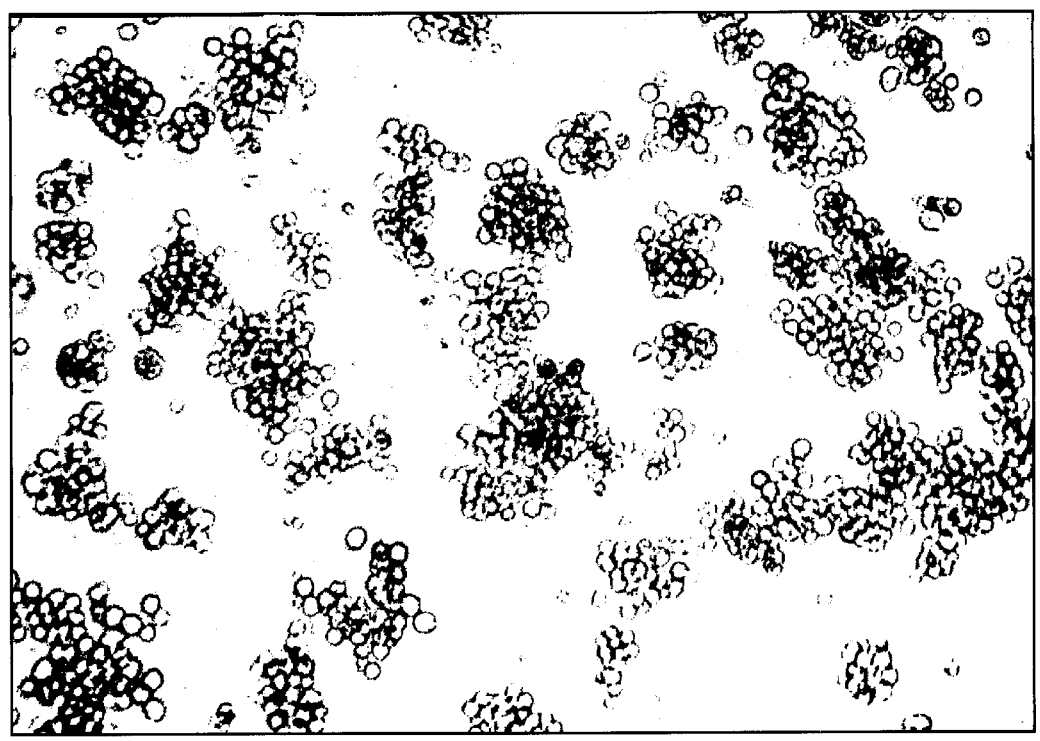
FIG. 4a Control Human Leukemic K562 Colony Differentiation.
Figure 4B:
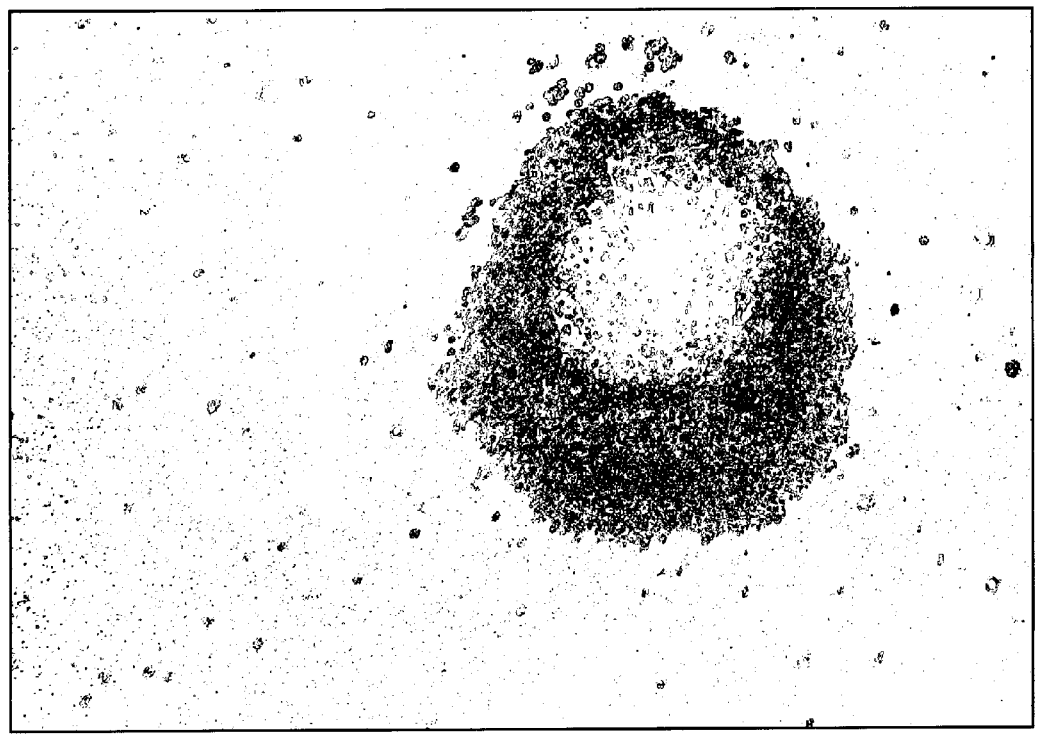
FIG. 4b Control Human Peripheral Blood Mononuclear Cell Colony Differentiation.
Figure 5:
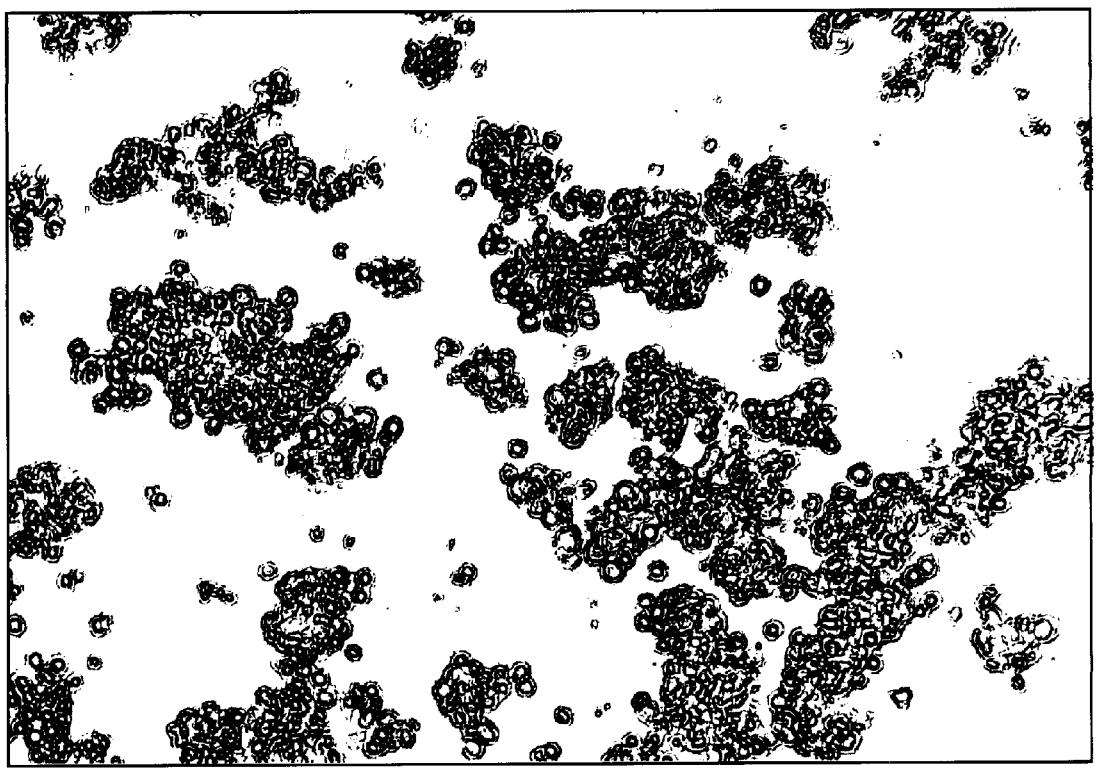
FIG. 5 Effects of 100% Oxygen Exposure on Human Leukemic K562 Colony Differentiation.
Figure 6A:
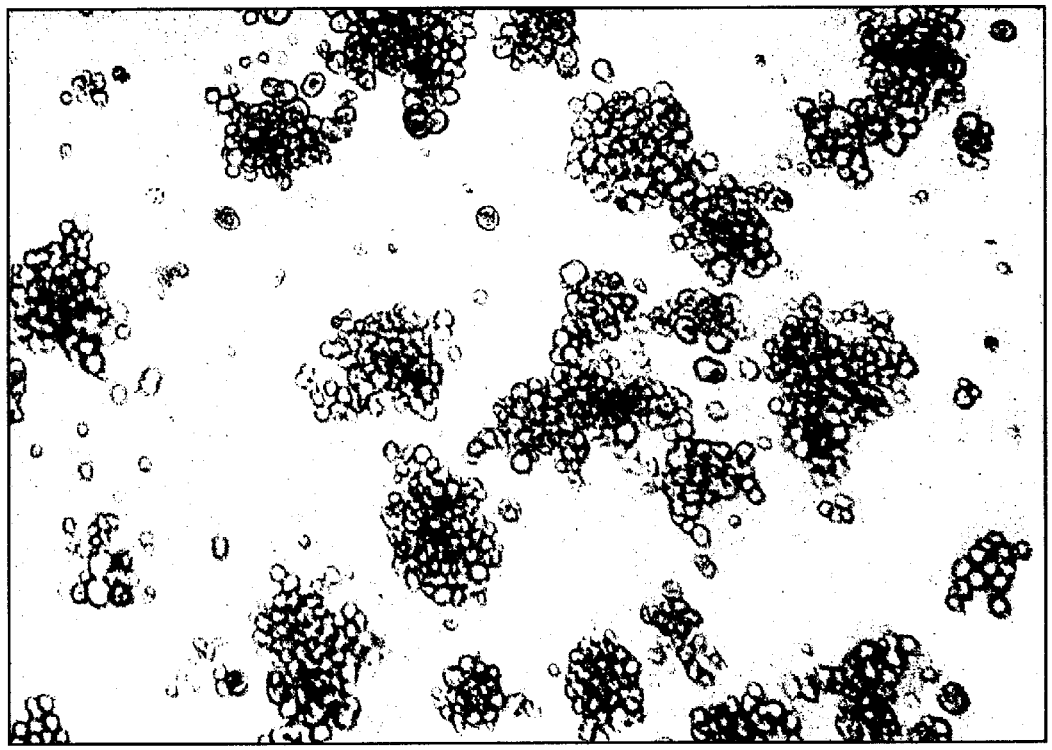
FIG. 6a Effects of Ozone Exposure for 1.5 minutes at 5 ug/ml on Human Leukemic K562 Colony Differentiation.
Figure 6B:
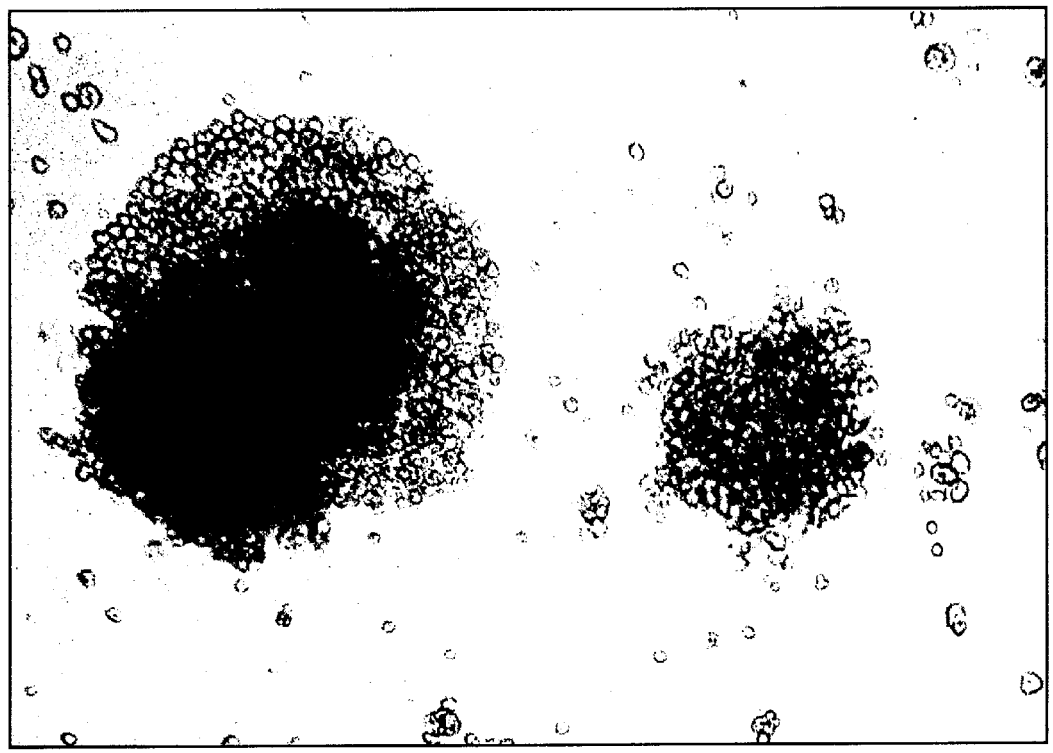
FIG. 6b Effects of Ozone Exposure for 1.5 minutes at 10 ug/ml on Human Leukemic K562 Colony Differentiation.
Figure 7A:
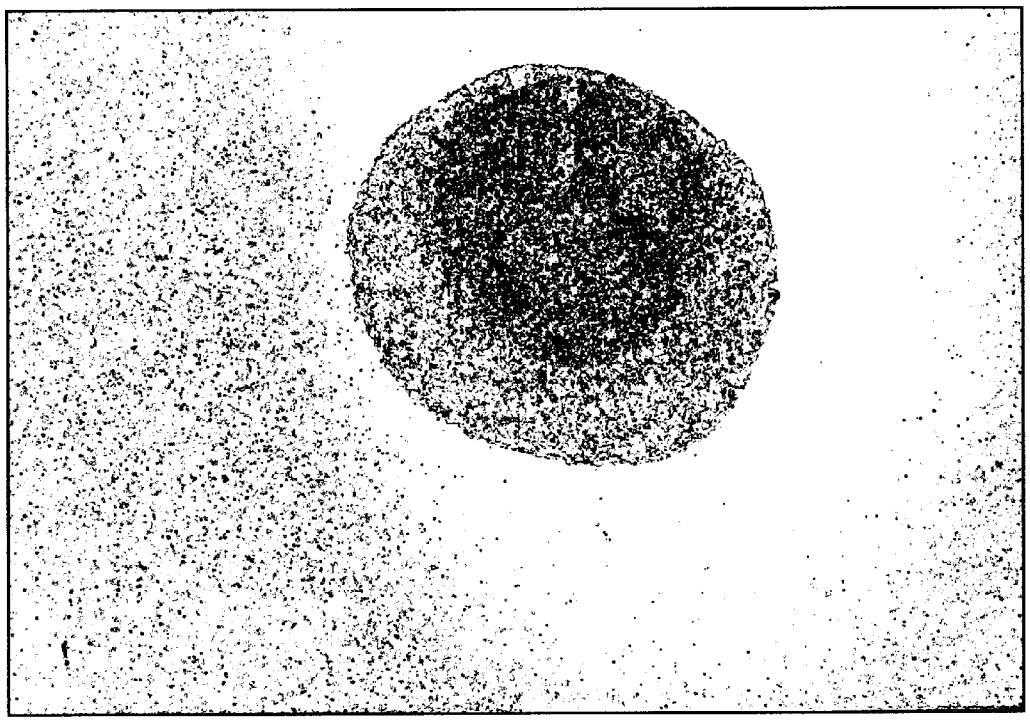
FIG. 7a Effects of Ozone Exposure for 1.5 minutes at 15 ug/ml on Human Leukemic K562 Colony Differentiation.
Figure 7B:
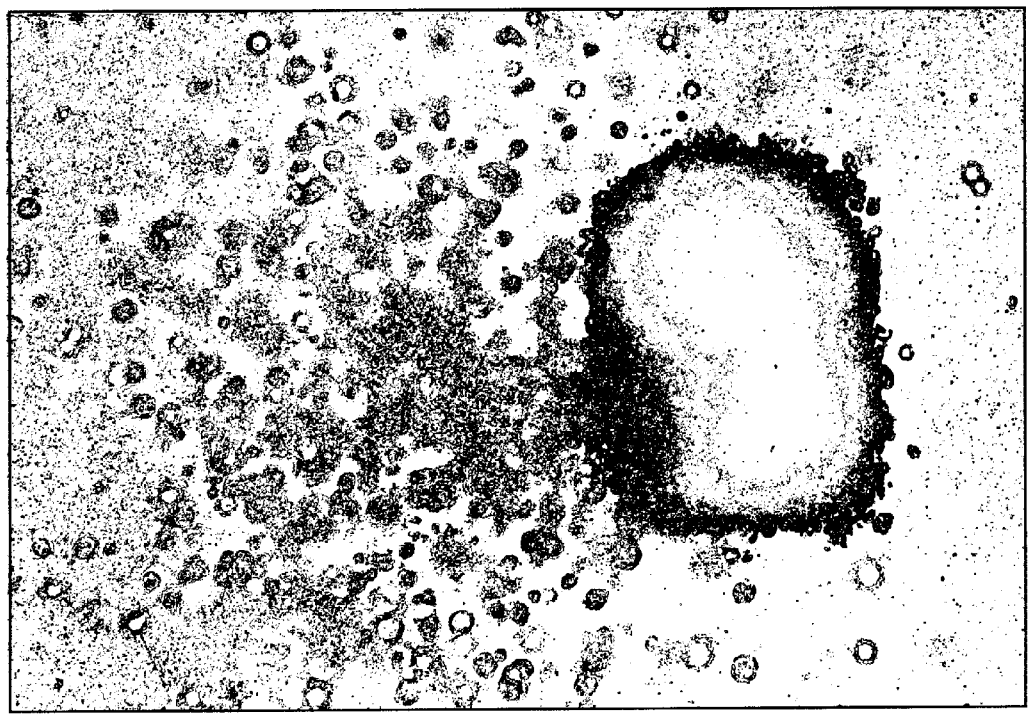
FIG. 7b Effects of Ozone Exposure for 1.5 minutes at 15 ug/ml on Normal Human Peripheral Blood Mononuclear Cell Colony Differentiation.
Figure 8A:
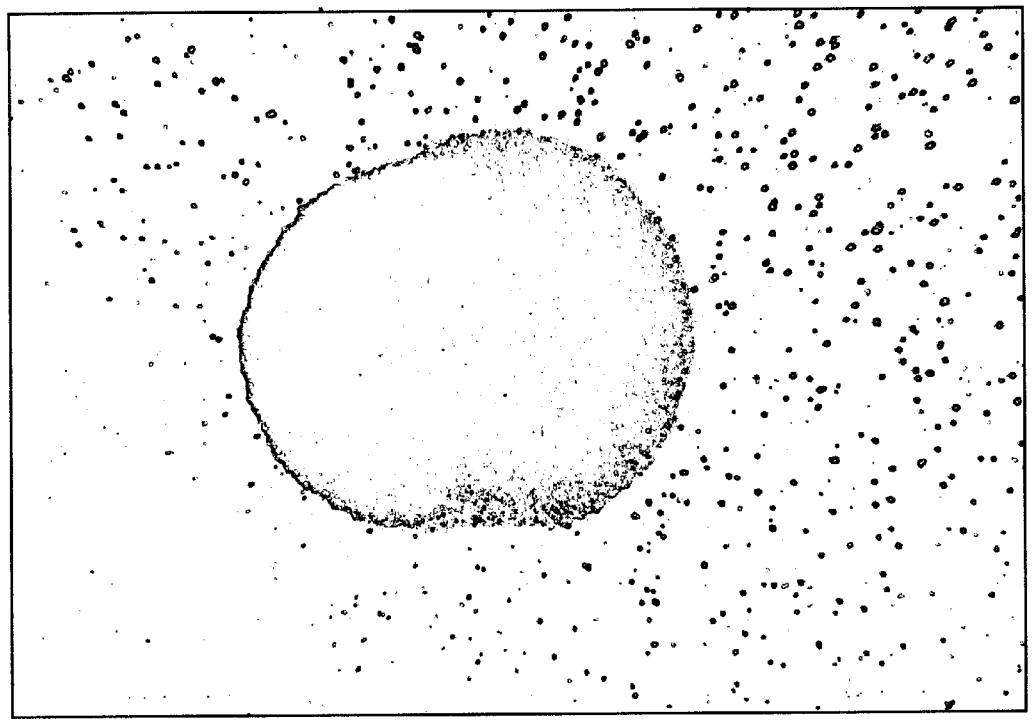
FIG. 8a Effects of Ozone Exposure for 1.5 minutes at 25 ug/ml on Human Leukemic K562 Colony Differentiation.
Figure 8B:
FIG. 8b Effects of Ozone Exposure for 1.5 minutes at 25 ug/ml on Normal Human Peripheral Blood Mononuclear Cell Colony Differentiation.

The results of the experiments show a reduction in the viability of malignant cells (K562, Human CML cell line) measured by Trypan blue exclusion as shown in FIG. 1. The results indicate that ozone or ROI's inhibits the proliferation of leukemia derived colonies with no deleterious effects in the colonies from normal human peripheral blood mononuclear cells (PBMC; FIG. 2). The evidence also shows that ozone or ROI's stimulates the production of normal hematopoietic colonies from a human K562 leukemic cell line as shown in FIGS. 3–8. These leukemic cell colonies are differentiated into the normal hematopoietic colonies, namely: colony forming units-erythroid (CFU-E), burst forming units-erythroid (BFU-E (primitive and mature)), granulocyte/monocyte-colony forming units (GM-CFU), and mixed colonies of granulocyte/erythroid/monocyte/megakaryocyte-colony forming units (CFU-GEMM; FIG. 3). Examination of control (non-ozonated) K562 leukemic cell colonies show no colony maturation or cell differentiation (FIGS. 3–4). The 100% oxygen treated K562 leukemic cells show similar results as those in the control leukemic cells as discussed above (FIGS. 3 and 5). The effects of ozone and ROI's show a dose response where increasing concentrations of ozone result in increased colony differentiation into normal cells (FIGS. 6–8). The experiments were run in parallel with normal human peripheral blood leukocytes. At the concentrations used, ozone shows no significant deleterious effects on normal human leukocytes. This is in agreement with prior publication concerning the effects of ozone on normal human leukocytes and whole blood (Bocci, 1995, Zee, U.S. Pat. No. 4,632,980).

I claim:

1. A method of promoting leukemic cells to differentiate into normal cells in a mammal by administering to said mammal in need thereof a leukemia therapeutically effective amount of ozone wherein said administering of said ozone is by a method selected from the following group consisting of:
    (a) direct injection of said ozone into said mammal;
    (b) ex vivo treatment of blood from said mammal with said ozone followed by reinfusion of said treated blood into said mammal;
    (c) injection of ozone treated products into said mammal;
    (d) inhalation of said ozone treated products;
    (e) insufflation of said ozone.

2. A method of promoting chronic myeloid leukemia cells to differentiate into normal cells in a mammal by administering to said mammal in need thereof a chronic myeloid leukemia therapeutically effective amount of ozone, wherein said administering of said ozone is by a method selected from the following group consisting of:
    (a) direct injection of said ozone into said mammal;
    (b) ex vivo treatment of blood from said mammal with said ozone followed by reinfusion of said treated blood into said mammal;
    (c) injection of ozone treated products into said mammal;
    (d) inhalation of said ozone treated products;
    (e) insufflation of said ozone.

3. A method of promoting leukemic cells to differentiate into normal cells in a mammal by administering a therapeutically effective amount of ozone so as to modulate said mammal's hematopoietic and immune systems wherein said administering of said ozone is by a method selected from the following group consisting of:
    (a) direct injection of said ozone into said mammal;
    (b) ex vivo treatment of blood from said mammal with said ozone followed by reinfusion of said treated blood into said mammal;
    (c) injection of ozone treated products into said mammal;
    (d) inhalation of said ozone treated products;
    (e) insufflation of said ozone.

4. A method as claimed in claims 1, 2 or 3 further comprising ozone's reactive oxygen intermediates.

5. A method as claimed in claim 4 wherein said ozone is administered such that its therapeutically effective concentration is maintained continuously in the blood of said mammal for the duration of the period of its administration.

6. A method as claimed in claim 4 wherein said therapeutically effective amount of ozone comprises from about 2 ml/kg of mammalian body weight to less than a toxic amount for a period for about 5 to 20 minutes.

7. A method as claimed in claim 4 wherein said therapeutically effective amount of ozone comprises from about 2 ml/kg of mammalian body weight to about 20 ml/kg of mammalian body weight for a period for about 5 to 20 minutes.

8. A method as claimed in claim 1 further administering a therapeutically effective amount of ether lipids.

9. A method as claimed in claim 8 wherein said ether lipid comprises alkyl-lysophospholipid.

10. A method as claimed in claim 4 wherein ozones reactive oxygen intermediates include reactive oxygen radicals.

11. A method as claimed in claim 10 wherein said reactive oxygen radicals impact on amino acids, and enzymes resulting in the inhibition of the protein tyrosine kinase.

12. A method of promoting leukemic cells to differentiate into normal cells and to mature from the leukemic blast cell stage by administering a therapeutically effective amount of ozone wherein said administering of said ozone is by a method selected from the following group consisting of:
    (a) direct injection of said ozone into said mammal;
    (b) ex vivo treatment of blood from said mammal with said ozone followed by reinfusion of said treated blood into said mammal;
    (c) injection of ozone treated products into said mammal;
    (d) inhalation of said ozone treated products;
    (e) insufflation of said ozone.

13. A method as claimed in claim 8 wherein said ether lipids provide an affinity for administering said ozone so as to enhance cellular differentiation of white blood cells.

14. A method as claimed in claim 6 wherein said ozone in said blood of said mammal modulates the hematopoietic and immune systems of said mammal.

15. A method as claimed in claim 5 wherein said level of white blood cells is lowered.

16. A method as claimed in claim 10 wherein said reactive oxygen radicals include superoxide anion radical.

* * * * *